United States Patent [19]
Mesek

[11] 3,975,222
[45] Aug. 17, 1976

[54] METHOD OF FORMING A FIBROUS WEB

[75] Inventor: Frederick K. Mesek, Downers Grove, Ill.

[73] Assignee: Johnson & Johnson, New Brunswick, N.J.

[22] Filed: Aug. 1, 1974

[21] Appl. No.: 503,830

Related U.S. Application Data

[62] Division of Ser. No. 377,351, July 9, 1973, Pat. No. 3,848,598.

[52] U.S. Cl. ............................. 156/62.2; 156/181; 156/276
[51] Int. Cl.² ......................................... A61F 13/16
[58] Field of Search ........................ 156/62.2–62.8, 156/90, 153, 163, 174, 175, 180, 181, 231, 242, 246, 276, 296; 161/64, 116, 124, 164, 169, 170, 177, 179–181; 162/100, 109, 188; 128/284, 287, 290 R, 290 P; 19/144.5, 155; 93/1 WZ; 264/109, 115, 116, 112, 113, 121

[56] References Cited

UNITED STATES PATENTS

| 850,151 | 4/1907 | Goldman | 156/62.8 |
|---|---|---|---|
| 3,612,055 | 10/1971 | Mesek | 128/287 |
| 3,682,761 | 8/1972 | Lee et al. | 161/169 |
| 3,729,005 | 4/1973 | Lee et al. | 128/287 |
| 3,763,863 | 10/1973 | Mesek et al. | 128/287 |
| 3,766,922 | 10/1973 | Krusko | 128/284 |
| 3,860,002 | 1/1975 | Kolbach | 161/116 |

FOREIGN PATENTS OR APPLICATIONS

| 928,270 | 6/1963 | United Kingdom | 156/62.2 |
|---|---|---|---|
| 1,145,618 | 3/1969 | United Kingdom | 128/284 |

*Primary Examiner*—Douglas J. Drummond
*Assistant Examiner*—John E. Kittle

[57] ABSTRACT

A method of producing a disposable diaper and the diaper produced thereby are disclosed. The disposable multi-layer diaper includes at one side a porous fibrous facing layer to be brought into contact with an infant's skin, and includes at the other side a water impervious backing sheet, with a double contoured cross-sectional batt being interposed between the facing layer and backing sheet. The batt is smoothly contoured by increased fiber content along the transverse and longitudinal medians from the edges to the center of the batt. The batt is positioned in face-to-face engagement with the backing sheet. The batt and lateral extremities of the facing layer which extend beyond the batt are each adhered to the backing sheet. In a preferred embodiment of the invention, a paper-like, densified, highly compacted cellulosic layer is formed integrally with the batt and is positioned in face-to-face engagement with the backing sheet.

The method provides a transverse peak in an air-laid web by simultaneously feeding to an individualizing station two continuous strips of compacted fibers, one strip being narrower than the other and lying along the longitudinal median of the other, the individualized fibers then being deposited on a moving foraminous belt from an air stream. Longitudinal peaks are provided by varying the rate of feed of the continuous strips to the individualizing station.

10 Claims, 8 Drawing Figures

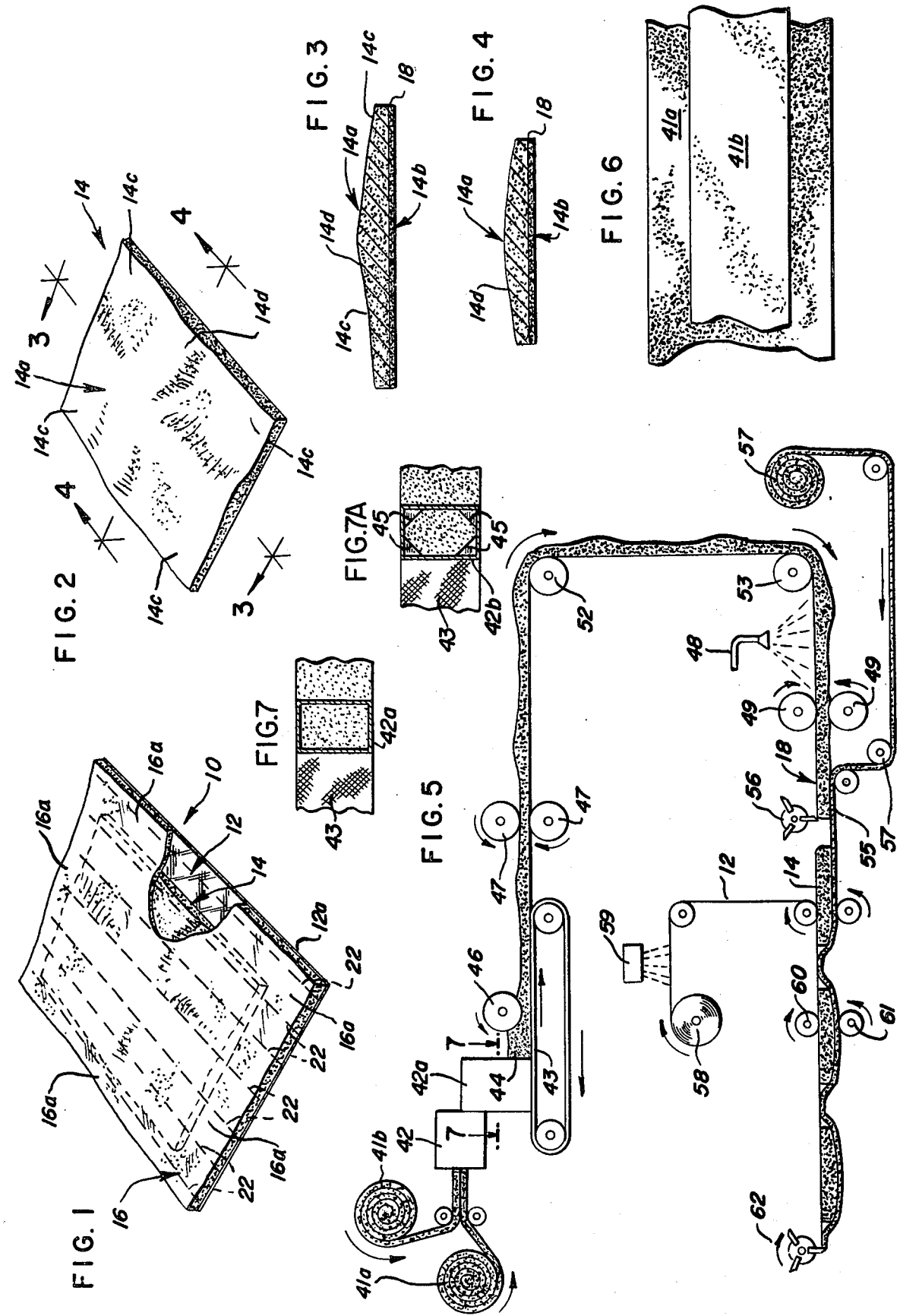

METHOD OF FORMING A FIBROUS WEB

BACKGROUND OF THE INVENTION

Disposable diapers have met with increasing commercial acceptance in recent years, primarily because of their convenience. Such diapers have conventionally included a facing layer to be brought into contact with an infant's skin, an absorbent panel adjacent thereto, and a water-impervious or a water repellent outer layer.

Known types of disposable diapers have had many functional deficiencies including inadequate absorptive capacity and inability to keep moisture away from the surface of the diaper which comes into contact with the infant's skin. Another serious drawback of prior art diapers is the tendency for liquid to leak around the edges of the diaper, particularly at night during periods of heavy discharge.

A significant advance in the art is provided by the diaper constructions disclosed and claimed in commonly assigned, Mesek et al., U.S. Pat. No. 3,612,055. The diaper structure illustrated therein includes, in order; a fibrous facing layer which is to be brought into contact with the infant's skin; an absorbent panel comprising a batt of highly porous, loosely compacted cellulose fibers having a paper-like, densified, highly compacted cellulosic fibrous layer integral with the loosely compacted batt; and an impervious backing sheet adhered to the densified layer portion of the batt throughout the interface therebetween. The facing layer is of porous construction and its fibers have less wettability for water than the fibers of the loosely compacted batt, resulting in a tendency for liquid to flow from the facing web into the batt. The densified fibrous layer has a smaller average pore size than the loosely compacted batt resulting in a tendency for liquid to flow from the batt into the densified layer.

In one embodiment of the diaper disclosed in the above mentioned patent, having particular utility during periods of heavy discharge, the absorbent panel of the diaper includes a relatively small second batt, similar to the batt already named, superimposed on the larger first named batt. This construction not only provides an increased absorptive capacity for the diaper, but also provides for greater compressibility at the center of the diaper because of the increased batt thickness. When the batt portion of the diaper is compressed by the infant's weight, the distances between adjacent fibers is decreased, i.e., there is a smaller effective capillary radius between adjacent fibers, particularly in the center section of the batt portion of the diaper. In consequence of this, there is a greater wickability at the more highly compressed center portion of the batt as compared to the less compressed marginal portions. This latter construction tends to keep liquid in place in the center portion of the diaper, and prevents it from leaking around the edges thereof.

In the last mentioned diaper embodiment, the integral densified layer portion of the larger batt is in face-to-face engagement with the backing sheet, thus helping the urine to spread laterally throughout the length and width of the batt beyond the edges of the smaller batt. The rapid spread of the urine by means of the densified layer is desirable, but carrying the liquid to the peripheral edges of the larger batt increases the likelihood of leakage at the edges of the diaper.

An improvement in multi-layer batt diapers is disclosed in commonly assigned copending, Mesek Application Ser. No. 187,248. The diaper structure utilized therein includes an absorbent panel consisting of two differently sized, superposed batt layers of highly porous, loosely compacted cellulose fibers, sandwiched between a porous facing layer and a water-impervious sheet, with the smaller of the batt layers being positioned adjacent the backing sheet, and with the larger batt layer being positioned over the smaller batt layer.

In this last mentioned embodiment, the added thickness provided by the smaller batt effectively confines large volume discharge of urine in areas out of contact with the infant's skin. However, due to the two-piece construction of the batt portions of this diaper, a large amount of cellulose fibers must be used, and this embodiment requires complex production apparatus to provide proper cutting and positioning of the two batts in registry with one another and the other components of the diaper.

SUMMARY OF THE INVENTION

The diaper of the present invention represents an improvement to the single batt, heavy discharge type of diapers by virtue of minimizing the likelihood of urine leaking from the edges of the diaper. To achieve this important result, the diaper of the present invention includes an absorbent panel consisting of a double contoured batt layer of highly porous, loosely compacted cellulosic fibers, sandwiched between a porous facing layer and a water impervious sheet.

In consequence of the construction of the diaper of the present invention, urine passes into the double contoured cross-sectional absorbent batt through the facing layer, flows preferentially into the densified layer of the batt to draw the liquid away from the infant's skin. Urine flowing into the densified layer tends to spread laterally because of its wicking action. The increased compressibility resulting from the double contoured cross-sectioned batt at the central portion of the diaper, combined with the compression caused by the infant's weight, provides for greater wickability at the longitudinal and transverse central portions of the diaper, so that there is a cooperative relationship with the densified layer which tends to concentrate urine away from the side edges of the diaper. Further, the non-contoured extremities of the batt (which have less cellulosic fibers than the contoured portion) provide, in effect, a barrier which also contributes to the retention of urine in the central portions of the diaper.

The construction of the diaper of the invention, as a whole, provides a mechanism for rapidly transporting urine from the point of discharge from the infant, and for spreading urine throughout most of the absorbent panel, while at the same time retarding the flow before the urine reaches the edges of the batt. It also provides a mechanism for holding urine discharge of limited content within the median portions of the diaper by a combination of a densified layer and a greater overall batt density in the median regions, provided by the action of the infant's weight on the double contoured cross-sectional portions of the diaper.

In addition to the advantages described above with respect to the handling of urine discharge by the diaper of this invention, it also provides enhanced structural stability, as compared to the above mentioned two-layer batt diapers which permit relative movement between the batts at their interface, as well as more efficient and easier production. The batt is directly adhered to the backing sheet (which is ordinarily the strongest structural element of the diaper), at the interface therebetween. Thus, the batt is positively anchored to the backing sheet against movement and against disintegration. The increased structural integrity is of special importance in a diaper that can hold a large volume of urine since the increased weight of the urine-saturated diaper subjects it, and particularly its relatively flimsy absorbent panel, to increased stress. Moreover, since the batt is integrally formed (as opposed to the two-layer batt panels of the prior art), there is no movement between the contoured cross-sectional medians and the marginal portions of the batt. Additionally, since the batt is a single unit, the amount of fibers which are used in a batt at a given maximum cross section is reduced, as compared to a two-layer batt construction, with a resulting decrease in production cost, and registration problems, inherent in the two layer batt diapers, are eliminated.

Moreover, the smooth contour of the batt provides better comfort and conformability for the infant than a two-piece batt diaper. The batt of the present invention provides a smooth contour at its surface rather than an abrupt change in thickness, as in a two-piece batt diaper which may produce a crease indentation in the infant's skin as his weight bears on the interface between the large and small batt. A two-piece batt diaper also tends to bend about the edges of the smaller batt as the diaper is positioned on an infant due to the uniform thickness of the larger batt and the cantilever bending effect generated therein. The contoured batt, however, bends uniformly due to its increasing thickness from the edges thus providing better conformability to the infant.

BRIEF DESCRIPTION OF THE DRAWINGS

FIG. 1 is a perspective view, with certain portions broken away, of an open unfolded diaper in accordance with an embodiment of this invention;

FIG. 2 is a perspective view of the double contoured cross section batt in accordance with this invention;

FIG. 3 is a cross sectional view taken along plane 3—3 of FIG. 2 illustrating the longitudinal cross section contour of the batt;

FIG. 4 is a cross sectional view taken along plane 4—4 of FIG. 2 illustrating the transverse contour of the absorbent batt;

FIG. 5 is a schematic view of an apparatus for forming the diaper of the present invention;

FIG. 6 is a plan view of two rolls of pulp board used to form the double contour cross section of the absorbent batt;

FIG. 7 is a schematic cross sectional view through plane 7—7 of FIG. 5; and

FIG. 7A is a schematic cross sectional view similar to FIG. 7 but illustrating another embodiment of the invention.

DETAILED DESCRIPTION

Referring to the drawings, and particularly to FIGS. 1 and 2, diaper assembly 10, when fully opened and laid out flat, comprises, in order, fibrous facing layer 16 adapted to be positioned adjacent the skin of an infant, absorbent fibrous panel, or batt 14, and a water-impervious sheet 12. Fibrous layer 16 is rectangular in shape, equal in dimension, and coterminous with backing sheet 12.

Batt 14 comprises a panel which is double contoured, i.e. centrally contoured in the transverse and longitudinal directions to produce a smooth peak on one major surface 14a. The other major surface 14b of the batt, which may be formed by a densified layer 18, as discussed below, (FIGS. 2, 3 and 4) is planar in configuration and is in juxtaposition with the backing sheet 12. The batt 14 is rectangular in shape, but smaller than backing sheet 12 and facing layer 16, and disposed centrally thereof. The marginal portions 12a and 16a (i.e., the portions extending beyond batt 14) of sheet 12 and facing layer 16, respectively, are in face-to-face engagement with one another. Backing sheet 12 is adhered to layer 14 and 16 at the interface therebetween, as will hereinafter be described.

In the preferred embodiment of the invention, moisture impervious sheet 12 is formed of polyethylene having a thickness of approximately 0.001 inch. The sheet may be smooth, or may be embossed to improve its drape and feel. Other suitable flexible moisture impervious sheets may be used in accordance with the invention, such as, for example, polyethylene terephthalate sheets having a thickness of about 0.0005 inch.

Batt 14 is formed of loosely compacted short cellulose fibers, such as wood pulp fibers, or cotton linters, or mixtures thereof, which are primarily held together by interfiber bonds requiring no added adhesive, as is known in the art. Briefly, this batt is a low bulk density coherent web of loosely compacted cellulose fibers, preferably comminuted wood pulp fibers in the form of so-called "fluff".

The term "short fibers," as used herein, refers to fibers less than about ¼ inch in length, in contrast to "long fibers," or "textile length fibers," which are longer than about ¼ inch in length, and generally are between about ½ and 2½ inches in length. The former are substantially less costly than the latter. The classification of fibers by length may be carried out by the Clark Classification procedure described in the test manual of The Technical Association of Pulp and Paper Industry (TAPPI-T233 SU64).

Paper-like densified layer 18 of batt 14 is formed by a slight moistening of one surface of the batt followed by the application of pressure thereto. The general nature of the batt and of its densified layer and the method of producing the same are described in U.S. Pat. No. 3,017,304, dated Jan. 16, 1962.

The composite density of batt 14 including the densified layer 18 of the batt, should be above about 0.07 gm./cc., and preferably between about 0.10 and 0.15 gm./cc. The foregoing density values are applicable to the diaper as produced. In storage and handling, the loft or thickness of the batt is increased to some extent, resulting in lowered densities.

Facing layer 16 is made up of a mixture of fibers consisting predominantly of short cellulosic fibers such as wood pulp fibers or cotton linters, in amounts of about 75 percent to about 98 percent, the balance being textile length fibers such as rayon. Short cellulosic fibers such as wood pulp fibers or cotton linters are substantially less expensive than textile length cellulosic fibers such as cotton and rayon, and this low cost is a factor in reducing the cost of the facing layer component of the diaper of this invention.

In facing layer 16, the short fibers are in uniform admixture with 2 percent to 25 percent by weight of textile length fibers, such as 1.5 denier rayon fibers uniformly cut to 1½ inches length. The short and long fibers are randomly and substantially uniformly dispersed and bonded with a bonding agent such as a self-cross linking acrylic emulsion. One bonding agent that has been applied with considerable success is a latex of a polyethyl-acrylate copolymer containing small amounts of acrylonitrile and a cross-linking monomer sold under the trademark HYCAR 2600 × 120. The bonding agent should be of the low viscosity type with a viscosity less than 5 centipoises. The facing layer is also treated with a wetting agent, such as, an anionic surfactant, to partially counteract the water repellency of the bonding agent and bring the facing layer to the desired degree of wettability. Typical surfactants which have been found to be suitable are the ionic sulfonated alkyl ester sold under the trademark TRITON GR-5 and the non-ionic polyoxyethylene sorbitan monolaurate sold under the trademark TWEEN 20. Facing layers of this character are described in greater detail in commonly-owned U.S. Pat. No. 3,663,348.

Facing layers suitable for use in this invention have fabric weights in the range of 1 to 5 oz./yd.$^2$ and densities less than 0.15 gm./cc., generally in the range between 0.05 and 0.1 gm./cc. The dry strength of the facing layer, for a fabric having a weight of about 1.5 oz/yd.$^2$, is at least 0.15 lbs./in. of width in the machine direction and at least 0.08 lbs./in. of width in the cross direction. The fabrics have unusually good elongation, loft, softness and drape characteristics in comparison to prior products incorporating any substantial amount of short fibers.

For a more detailed description of facing layers and the methods of producing them, reference may be made to the above mentioned U.S. Pat. No. 3,612,055, the disclosure of which is hereby incorporated herein in its entirety by this reference.

Alternatively, the facing layer may be an apertured nonwoven fabric formed, for example, in accordance with the teachings in commonly assigned U.S. Pat. Nos. 2,862,251, 3,081,514 and 3,081,515, the disclosures of which are expressly incorporated herein by this reference. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well understood by those skilled in the art. A suitable binder may be utilized to help retain the fibers in their rearranged locations, as is also well understood by those skilled in the art. The fabric can be made of naturally occurring fibers, synthetic fibers or blends thereof. Typical facing layers made of a polyester material may have a weight of ¾ oz./yd.$^2$ In instances where the foramina are relatively large and particularly when the facing is formed of a polyester material, a layer of tissue or the like may be interposed between the facing layer and the batt to prevent the short paper-making fibers of the batt from sifting through the facing.

It should be understood that the facing layer may also be formed of nonapertured material, such as a nonwoven isotropic web, sponge, or the like.

In all of the aforementioned facings, the materials should be relatively hydrophobic so as to retard wicking within the facing layer.

As is explained in U.S. Pat. No. 3,612,055, an important aspect of the improved diaper is the provision for selective wettability among the above described fibrous components, such that the moisture is selectively drawn from the facing layer into the body of the batt and then from the body of the batt into the densified layer thereof. Specifically, when liquid, such as urine, flows into a small area on the outer surface of facing layer 16, it flows preferentially into underlying batt 14 rather than to other areas of the facing layer, thus tending to restrict wetting in the facing layer to a small area and to move the liquid away from the infant's skin.

When an infant's weight rests on the aforedescribed diaper construction having the double contour batt, there is a tendency for the uncompressed absorbent material of the batt 14 to be compressed by the weight. Since there is a greater thickness of material in the longitudinal and transverse central portions of the diaper than at the margins thereof, there will be greater pressure (and hence more compression) at the center. This results in a smaller effective capillary radius in the central section, and greater wickability of the more highly compressed center portion as compared to the less compressed marginal portions 14c. As a result, urine passing into the central portion of batt 14 tends to flow preferentially into the underlying portions of the batt, rather than into the marginal portions 14c of the batt.

The liquid which flows through batt 14 flows preferentially into underlying densified layer 18, rather than to other areas of the loosely compacted batt, thus tending to move the liquid farther from the infant's skin. The liquid flowing into densified layer 18 tends to spread laterally because of its wicking action, and liquid which might pass through the densified layer during discharge (when flow is rapid) is held back by the impervious backing sheet for sufficient time to permit absorption to take place.

Since the densified layer is confined to the central portion of the diaper, the capacity of the diaper to retain and confine liquid in this area, as compared to prior art diapers, is markedly improved. Liquid in excess of the absorptive capacity of densified layer 18 is forced back by impervious sheet 12 into the dry portion of loosely compacted batt 14, thus utilizing the additional absorptive capacity therein. It will be appreciated that liquid will initially flow into the dry portions of the relatively highly compressed central contoured portions of batt 14 before it flows into the less highly compressed marginal portions 14c thereof. The net result is that the loosely compacted marginal portions 14c act as dam-like barriers that cooperate with the densified portion 18 of batt 14 to confine liquid at the central portions of the diaper. Only after the relatively highly compressed central portions of batt 14 become saturated will liquid flow into the marginal portions 14c, and thus it will be appreciated that the diaper of the present invention effectively minimizes the likelihood that liquid will escape around the edges of the diaper.

As noted above, because of the increased absorptive capacity provided by the double contoured batt construction, the aforedescribed diaper is especially adapted for use during periods of heavy discharge. In previous types of heavy duty type diapers, problems have been encountered in retaining the various batt layers in place when the diaper becomes saturated, since the increased weight attributable to the larger absorbed volume subjects the diaper to increased stresses not normally encountered in a diaper having a smaller absorptive capacity. This problem is particularly acute, since the loosely compacted fibrous layers that are conventionally used as the absorbent panel of the diaper are usually relatively flimsy and weak when compared to the facing layer and particularly to the backing layer, which ordinarily has much greater structural integrity than the other layers of the diaper.

The diaper of the present invention obviates the problems noted in the preceding paragraph by having the absorbent panel and the facing layer adhered to the backing sheet substantially throughout the interface therebetween. With reference to FIG. 1, it will be noted that parallel lines of adhesive 22 are utilized to adhere the densified layer 18 or batt 14, as well as the marginal portions 16a of facing layer 16, to the backing sheet 12. Other adhesive patterns may be utilized, as will occur to those skilled in the art. In any event, since batt 14 in its entirety is secured to backing sheet 12, the batt is firmly anchored in place against movement and against disintegration.

The diaper of this invention may be prepared as schematically shown in FIG. 5. Two rolls of compacted wood pulp 41a and 41b are provided to feed a source of short cellulosic fibers to grinding mill 42 from which a stream of fibers is blown downwardly through duct 42a onto belt 43 as a layer 44 weighing between about 2 and about 10 oz./yd.$^2$. Duct 42a is substantially rectangular in cross section, as shown in FIG. 7.

To produce the contoured cross section across the web, as discussed above, two rolls of compacted wood pulp may be used. Roll 41a corresponds to the width of the batt 14 to be formed, and roll 41b is narrower than 41a to provide the transverse contour (see FIG. 4). During the grinding operation, rolls 41a and 41b are co-mingled to produce the smooth contoured cross section, as illustrated in FIG. 4.

The contoured cross section across the web may also be produced by several other methods. One such method comprises feeding a source of fibers to a grinding station connected to a duct equipped with baffles at its exit to allow more fibers to be concentrated at the central portion of the web. FIG. 7a illustrates such a duct 42b and shows baffles 45 which eliminate the corners of the rectangle from the available duct area. Another method of producing a contoured cross section across the web comprises: grinding fibers at one station and depositing them to produce a continuous web at the maximum width desired and grinding fibers at another station and depositing them downstream along a band of lesser width of top of and along the median of the first-named continuous web.

The longitudinal contour, as illustrated in FIG. 3, is achieved by the grinding mill by varying the speed at which the fibers from rolls 41a and 41b are deposited on belt 43. By decreasing the depository rate, the marginal areas of reduced thickness 14c are produced and, correspondingly, by increasing the depository rate the thickened central contour portion 14d is produced.

Alternatively, the longitudinal contour may be achieved by (1) varying the speed of the belt segment on which the fibers are deposited, or by (2) grinding fibers at one station to produce a continuous web with a transverse contour and then sequentially grinding selected amounts of fibers at another station which are deposited on the continuous web to produce repetitive longitudinal contours.

The contour thickness is preferably formed to provide a ratio of apex thickness to corner thickness in the range of 1.5 to 4.

Mill 42 grinds the pulp boards into individual short fibers. However, in one preferred embodiment, some of the pulp board fibers are not completely comingled and remain joined to other fibers in small clumps, generally smaller than about ¼ inch across. It has been found that the presence of such small clumps of fibers in the body of the batt 14 provides islands of increased tenacity for holding liquid. When an infant's weight on one portion of the batt densifies that portion, it tends to concentrate liquid in the densified portion, the presence of the clumps of fiber elsewhere in the batt tends to hold the liquid in place. Preferably from about 2 to about 10 percent of the fibers should be in the form of such clumps.

The air blown contoured layer is then passed under compacting roll 46 from which it emerges with enough integrity to sustain itself as a web without the support of belt 43. The web then passes through a pair of calendar rolls 47 for further compression and then around rollers 52 and 53 which reverse the orientation of the web so that the planar surface is facing upwardly. The web then passes under nozzle 48 which deposits a fine spray of moisture on the upper surface of the web. The moistened web then passes between another set of calendar rolls 49 which exert heavy pressure on it to form a skin 18 upon its upper surface.

The amount of moisture applied to the web may vary suitably from about 0.0005 to about 0.03 cc. of water per square centimeter of web surface, depending upon the thickness of the paper-like densified skin 18 desired, with lesser amounts of moisture being used for thinner webs and very thin, papery skin and greater amounts for thicker webs and skins of greater thickness. The amount of pressure applied by rolls 49 may vary from about 5 to about 100 pounds per square inch, with the commercially preferable range being from about 10 to about 50 pounds per square inch. In a typical embodiment, the web is sprayed with about 0.0015 cc. of water per square centimeter of web surface and subjected to a pressure of about 40 pounds per square inch to obtain a densified, coherent papery skin of uniform thickness on the surface of the web which has been moistened.

In the absorbent web and in the batts cut therefrom, there are weak hydrogen bonds in the loosely compacted body of the batt providing sufficient strength to maintain the integrity of the batt in ordinary handling, and there are strong hydrogen bonds in the densified layer of skin to increase the cohesive strength of the composite. After the skin is formed, the absorbent web comes into contact with a web of facing material 55 and is supported thereby while being cut by cutter 56 into individual batts 14. The facing material is fed from rolls 57.

Polyethylene film 12 is fed to the assembly from roll 58, lines of adhesive being applied from applicator 59. As described above, the adhesive is applied as parallel lines of beads 22 between the impervious sheet 12 and the densified layer 18 of the batt (or the facing layer in the marginal portion of the diaper). Adhesive may, if desired, by applied as a continuous layer between the polyethylene and the batt, but such application tends to provide excessive stiffness. The adhesive may also be applied in other patterns, such as spaced dots or other forms of so called "island" bonds, but fairly close overall adhesion between the sheet and the batt is required and no portion of the polyethylene should be more than about 2 inches from a point of adhesion. In the absence of such overall adhesion, polyethylene film 12 may be separated from the densified layer 18 to create substantial spaces in which uncontrollably large amounts of liquid urine can accumulate. After the facing material 16 and polyethylene 12 are brought into contact with opposite faces of the absorbent batts, the assembly is subjected to compression by rolls 60 and 61 to shape the diaper assembly, and the individual diapers are cut off by cutter 62.

If desired, adhesive applicator 59 may be omitted and adhesion between the polyethylene layer and the fibrous layers may be achieved by heat sealing, employing a suitable sealing element in the production line.

The diaper is normally packaged and sold in a folded condition, as is described in detail in the above mentioned U.S. Pat. No. 3,612,055. Briefly, the opposite sides of the diaper are folded inwardly toward one another, with the folded portions then being folded outwardly to provide a three-ply arrangement. The folded over portions are adhered to the main body of the diaper by centrally disposed spots of adhesive, and when it is desired to use the diaper, the folds of the diaper are opened on opposite sides of the adhesive spots, and the end portions of the diaper are placed around the waist of the infant. The overlapping corners of the end portions of the diaper are secured together by pinning, or by adhesive strips that may be attached to the backing sheet 12.

It will be understood by those skilled in the art that variations and modifications of the specific embodiments described above may be employed without departing from the scope of the invention as defined in the appended claims.

What is claimed is:

1. The method of forming a fibrous web from which sections may be cut to form batts, said web being characterized by increasing quantities of fibers from the side edges to the central portion of the web and by alternately increasing and decreasing quantities of fibers along the length of the web, including the steps of providing at least two continuous strips of compacted short cellulose fibers, one strip being smaller in width than the other strip and located along its longitudinal median; simultaneously individualizing the fibers from each strip at a single individualizing station to produce a single stream of fibers of increasing and decreasing fiber content transversely across said stream; air laying said fibers on a moving foraminous belt to form a web with a planar surface adjacent to said belt and a widthwise convex surface at the opposite surface; and at substantially the same time sequentially varying the rate of fiber deposition as the formed web is carried by said foraminous belt while maintaining said convex surface thereby to produce a web with longitudinal and transverse sections of alternately increasing and decreasing fiber content.

2. The method as set forth in claim 1 wherein said rate of deposition is varied by alternately increasing and decreasing the rate at which said strips of compacted fibers are fed to said individualizing station.

3. The method as set forth in claim 1 wherein said rate of deposition is varied by alternately increasing and decreasing the speed of said foraminous belt.

4. The method as set forth in claim 1 further comprising the steps of spraying said planar surface with water and compressing said wetted web to form a densified compacted layer at said planar surface.

5. The method as set forth in claim 1 further comprising the steps of cutting said web at positions of decreasing fiber quantities along the length thereof to produce said batts, providing for each of said batts a porous facing layer wider than said batt; positioning said batt centrally of said facing layer with said planar surface opposite said facing layer; providing an inpervious backing sheet substantially coextensive with said facing layer; and adhering said backing sheet to the planar surface of said batt and the marginal portions of the facing layer extending beyond the batt.

6. The method of forming a fibrous web from which sections may be cut to form batts, said web being characterized by increasing quantities of fibers from the side edges to the central portion of the web and by alternately increasing and decreasing quantities of fibers along the length of the web, including individualizing short cellulose fibers from at least one fiber source; air laying said individual fibers on a moving foraminous belt in a manner to produce a web having a greater depth of fibers along the median of said belt as compared to the sides of the belt and at substantially the same time sequentially varying the rate of deposition of said individualized fibers onto said belt to produce a web with longitudinal and transverse sections of alternately increasing and decreasing fiber content.

7. The method of claim 6 wherein said individualized fibers are deposited on said moving foraminous belt after passage through a duct which has a discharge end overlying said belt, said duct having a cross-sectional configuration which provides a longer passage under said discharge end of said duct for the mid-portion of said belt than for the marginal portions thereof.

8. The method of claim 6 wherein said individualized fibers are deposited on said moving foraminous belt at two locations, one location being downstream of the other, the fibers being deposited at one location at the maximum width desired in the web and being deposited at the other location along the median of the web.

9. The method of claim 8 wherein said one location is upstream of said other location.

10. The method of claim 6 wherein a web having a greater depth of fibers along the median of said belt as compared to the sides of said belt is laid by exposing the median of said belt to said air laying for a longer period than the sides of said belt are exposed to said air laying.

* * * * *